US012478193B2

(12) United States Patent
Jiménez Castillo

(10) Patent No.: US 12,478,193 B2
(45) Date of Patent: Nov. 25, 2025

(54) RESTING ELEMENT WITH CONNECTION TO THE EARTH CONNECTION OF THE DWELLING

(71) Applicant: Maria Rosario Jiménez Castillo, Belicena (ES)

(72) Inventor: Maria Rosario Jiménez Castillo, Belicena (ES)

( * ) Notice: Subject to any disclaimer, the term of this patent is extended or adjusted under 35 U.S.C. 154(b) by 470 days.

(21) Appl. No.: 17/786,834

(22) PCT Filed: Jan. 13, 2021

(86) PCT No.: PCT/ES2021/070011
§ 371 (c)(1),
(2) Date: Oct. 21, 2022

(87) PCT Pub. No.: WO2021/144489
PCT Pub. Date: Jul. 22, 2021

(65) Prior Publication Data
US 2023/0218092 A1 Jul. 13, 2023

(30) Foreign Application Priority Data
Jan. 16, 2020 (ES) .................................... 202030057

(51) Int. Cl.
*A47C 31/00* (2006.01)
*A47C 27/12* (2006.01)
*A61N 1/14* (2006.01)

(52) U.S. Cl.
CPC .......... *A47C 31/004* (2013.01); *A47C 27/122* (2013.01); *A61N 1/14* (2013.01); *A47C 31/007* (2013.01)

(58) Field of Classification Search
CPC ... A47C 27/122; A47C 27/121; A47C 27/002; A47C 31/004; A47C 31/007;
(Continued)

(56) References Cited

U.S. PATENT DOCUMENTS

2015/0265063 A1 9/2015 Cappadona et al.

FOREIGN PATENT DOCUMENTS

CN 205454205 U * 8/2016 ........... A47C 31/004
CN 206295378 U * 7/2017
(Continued)

OTHER PUBLICATIONS

Acuna C.D., et al., "Estudio Polisomnográfico y Bioquímico Del Efecto Del Reposo Controlado en el Organismo Humano," Biovital Group, 6 pages.
(Continued)

*Primary Examiner* — Justin C Mikowski
*Assistant Examiner* — Deborah Talitha Gedeon
(74) *Attorney, Agent, or Firm* — Thomas Joseph

(57) ABSTRACT

The invention relates to a resting element with connection to the earth connection of the dwelling, of the type comprising a mattress topper, a bed base, and a latex mattress; where the topper has a means for connecting to the mattress and this, in turn, to the bed base, which finally connects to the earth connection of the dwelling via a universal connection system that incorporates a safety system to avoid overloading the line; and wherein the sheath incorporates a mesh of gold, silver, and organic graphite and silver filament which, together with the connection with the rest of the elements, improves its residual discharge and insulating capacity.

13 Claims, 1 Drawing Sheet

(58) Field of Classification Search
CPC ....... A47C 17/46; A47C 27/12; A47C 27/125; A47C 27/127; A47C 14/46; A61N 1/14
See application file for complete search history.

(56) References Cited

FOREIGN PATENT DOCUMENTS

| | | | | | |
|---|---|---|---|---|---|
| CN | 107280330 | A | * | 10/2017 | ........... A47C 29/003 |
| CN | 108099292 | A | | 6/2018 | |
| CN | 108300359 | A | * | 7/2018 | |
| CN | 108784121 | A | * | 11/2018 | |
| EP | 2103233 | A1 | | 9/2009 | |
| ES | 1058937 | U | | 2/2005 | |
| ES | 2574355 | B1 | | 3/2017 | |
| GB | 2439828 | A | * | 1/2008 | ........... G01N 29/022 |
| KR | 20180071901 | A | | 6/2018 | |
| WO | 2008087225 | A1 | | 7/2008 | |
| WO | WO-2015001165 | A1 | * | 1/2015 | ........... A47C 31/004 |
| WO | WO-2017140931 | A1 | * | 8/2017 | ............. A47C 17/46 |

OTHER PUBLICATIONS

BioVital, Informacion cientifica, Estudio I, Universidad de medicina de Granada, 55 pages.
BioVitalbeds, Primer Premio Internacional, “Investigacion Anti Aging” “Producto Anti Aging” Sociedad Espanola, De Medicina Estetica, Dossier Corporativo, 28 pages.
Discovery D Salud, “They Design a Bed Set That Protects from Electromagnetic Radiation”, Oct. 2006 (Spanish), 10 pages.
Informe Realizado Por la Fundación Europea de Bioelectromagne-Tismo y Ciencias de la Salud Sobre Los Efectos Biosaludables de la Cama Biovital, 2 pages.
International Search Report and Written Opinion for Application No. PCT/ES2021/070011, mailed on Apr. 16, 2021, 13 pages.

* cited by examiner

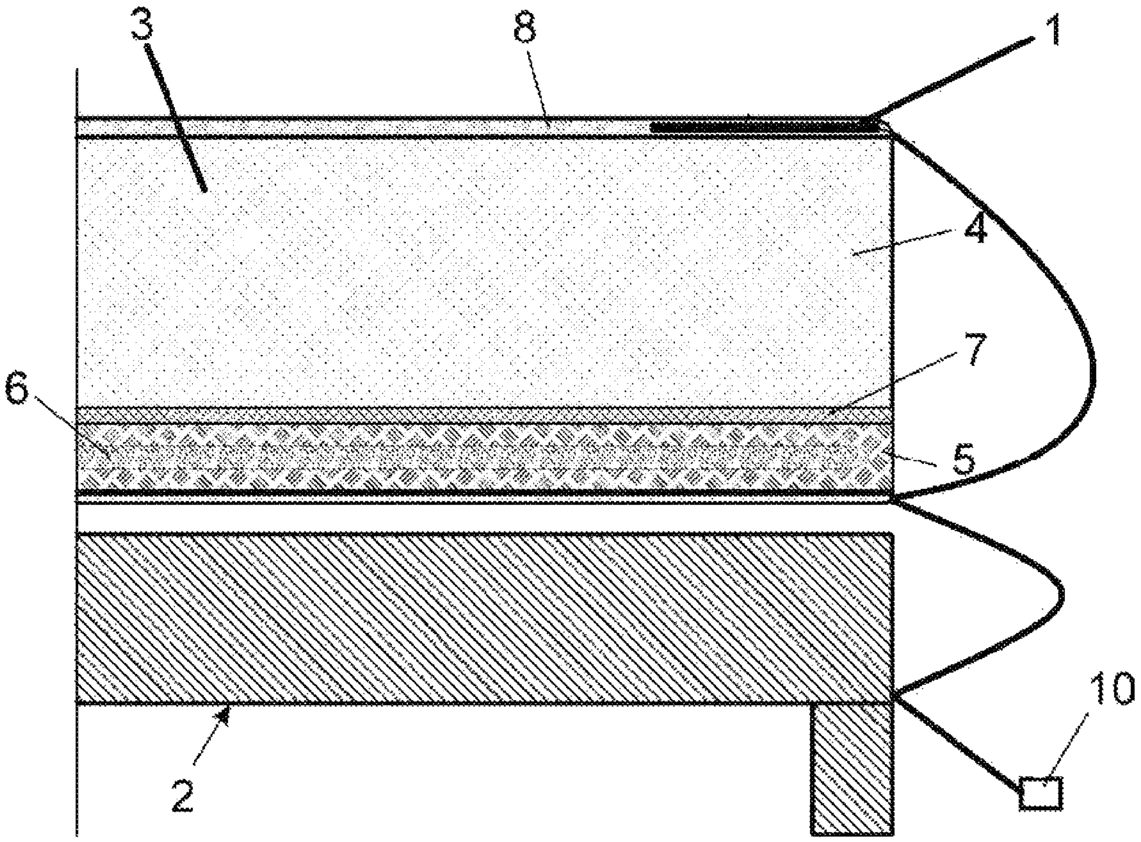
3
8
1
4
7
6
5
10
2

RESTING ELEMENT WITH CONNECTION TO THE EARTH CONNECTION OF THE DWELLING

CROSS REFERENCE TO RELATED APPLICATION

The present application is a U.S. national stage application of PCT International Application No. PCT/ES2021/070011, filed Jan. 13, 2021, and published as PCT Publication WO/2021/144489 on Jul. 22, 2021, which claims priority to Spanish Patent Application No. 202030057, filed Jan. 13, 2020. The disclosures of all the foregoing applications are hereby incorporated by reference in their entirety into the present application.

OBJECT OF THE INVENTION

The object of the present report is an element of rest with connection to the earth connection of the house, consisting essentially of a bed base of laminated vaporized beech wood, with 100% natural water-based varnish, and mattress with latex core, made of emulsion of the resin of the Hevea *brasilensis* tree, 100% natural, beaten and baked in oven at 120 degrees, without chemical additives, which incorporates an anti-humidity ionizing sheet of vaporized and pressed coconut 100% natural, with a central layer of pink salt rocks and white quartz, an antibacterial mesh of bamboo thread and a cover made of 70% cashmere and 30% organic cotton fabric, with a 4 cm filling in at least the upper part of the mattress, made of 100% natural wool and organic graphite and silver fabric and an aluminum plate associated with an earthing device; and where, in turn, the present invention incorporates an addition of graphene at the edge of the bed base and at the bottom of the mattress, together with three platinum antennas as ionizers, and finally, a new mesh fabric of gold, silver and/or graphite filament, which increase its conductive capacity.

BACKGROUND TO THE INVENTION

Nowadays, one of the fields that is becoming more and more important in the domestic sphere is the fact of how to achieve a better physical and/or mental state through a correct rest, as a consequence (among others) of a correct ionization of the home environment.

Various human activities and electrical applications produce positive ions, which cause the deterioration of our physical and emotional well-being. The excess of these positive ions, produced by chemical and electromagnetic pollution, is a primary cause of, among other things, increased stress, which in turn can lead to insomnia, migraines, exhaustion, hypertension, depression and aggravate asthma and respiratory allergies.

As a consequence of this, and essentially seeking to improve the quality of rest, the applicant is in turn the holder of the invention protected by Spanish patent ES 2 574 355, which describes a rest set for the recovery of the geo-electric field, consisting of a bed base made of laminated vaporized beech wood, with 100% natural water-based varnish, and a mattress with a latex core, made of emulsion from the resin of the Hevea *brasilensis* tree, 100% natural, beaten and baked in an oven at 120 degrees, without chemical additives, incorporating an anti-humidity ionizing sheet of 100% natural steamed and pressed coconut, with a central layer of pink salt rocks and white quartz, an antibacterial mesh of bamboo thread and a cover of 70% cashmere and 30% organic cotton fabric, with a 4 cm filling in at least the upper part of the mattress, of 100% natural wool and organic graphite and silver fabric and an aluminum plate associated with an earthing device.

This invention provides innumerable advantages by tackling the problem described in terms of the ionization of the environment, without having to resort to electrical devices which, although they can partially solve the technical problem posed, produce another series of problems associated with it.

The applicant is also aware of international application PCT/ES2007/000013 which describes a therapeutic rest bed, comprising a bed base with beechwood slats attached to the frame in mobile groups of two or three slats, depending on the areas of the body to which they correspond, by means of pivoting parts, shock-absorbing supports, height-adjustable supports and clamps, a 100% natural latex mattress with holes and a coconut fibre sheet, a mattress cover with organic carbon mesh connected to an earthing conductor, a mattress cover with another organic carbon mesh, a blanket with a merino wool cover with a thermo-regulating effect and a pillow, also made of 100% natural latex.

Likewise, he is aware of the existence of utility model ES 1 058 937 which describes a bed with slatted bed base and mattress; of a kind comprising a bed base provided with transverse slats for the support of the mattress and a mattress intended to rest on those slats to form a sleeping surface, characterized in that: the bed base comprises: an outer frame, an inner frame, a group of slats positioned in correspondence with the head support zone and mounted on the inner frame by means of elastic pieces of natural rubber; a group of slats positioned in correspondence with the shoulder support zone and mounted on the inner frame by means of elastic pieces of natural rubber attached to shock-absorbing supports; a group of double slats, with adjustable flexion, located in the back support area and mounted on the inner frame by means of elastic pieces of natural rubber; a group of slats located in the lumbar support area and mounted on the inner frame by means of elastic pieces of natural rubber attached to height-adjustable supports; and, a group of slats located in the leg support area and supported on the inner frame by means of elastic pieces of natural rubber; the mattress comprises: an inner core composed of a prismatic block of 100% natural latex with a plurality of holes of different diameters that define zones of different resistance and a lower layer of coconut fibre; an inner cover of cotton fabric; and an outer cover with an inner padding of merino wool and an organic carbon fabric to which an outer earthing conductor is connected, the free end of which ends in a piece of conductive material, such as copper or similar, for earthing.

With the aim of continuously improving the solutions to this problem, the applicant has made a series of improvements to the invention protected by Spanish patent ES 2 574 355, namely the presence of a new system or means of energy discharge through the connection between the elements that make up the rest element with connection to the earth of the dwelling, through an improved universal connection system adapted for discharge, which will allow this energy to be safely discharged to the earth, avoiding overloads in the system.

DESCRIPTION OF THE INVENTION

The technical problem solved by the present invention is to obtain a means of rest (a bed or similar) that includes means for the recovery of the terrestrial magnetic field for its safe transfer to the earth connection of the dwelling, avoiding possible overloads in the system. For this purpose, the rest element with connection to the earth connection of the dwelling, which is the subject of the present report, comprising a toper or mattress topper, a bed base and a latex mattress; said bed base being made of laminated vaporized beech wood, varnished with 100% natural water-based varnish, and a mattress made of a latex core, composed of an emulsion of the resin of the Hevea *brasilensis* tree, 100% natural, beaten and baked in an oven at 120 degrees Celsius, without any chemical additives, which, without any chemical additives, is made of latex, without any chemical additives, which, in addition, incorporates an ionizing and anti-humidity layer of steamed and pressed 100% natural coconut, with a central layer of pink salt rocks and white quartz rocks, as well as an antibacterial mesh of bamboo thread; and because the said mattress also has a cover made of a fabric made of 70% cashmere and 30% organic cotton, with a filling that covers at least the upper part of the mattress with a thickness of about four centimeters, made of 100% natural wool. Characterized in that the toper has a means of connection to the mattress and this, in turn, to the bed base, which is finally connected to the earth connection of the home through a universal connection system that incorporates a safety system to avoid overloading the line; and because the cover incorporates a mesh of gold, silver and organic graphite and silver filament which, together with the connection with the rest of the elements, improves its residual discharge and insulating capacity.

Thanks to its design, the rest element recommended here uses materials that serve to alleviate the technical problem posed, improving the user's rest, and where, one of the aspects of vital importance is the presence of a body or graphene element on the edge of the bed base or bottom of the mattress, which will be connected to the toper or mattress topper; and in this way they will be connected in turn with the bed base that includes the earth connection connected to the earth connection of the house.

The mattress has three platinum antennas in its structure, which will serve as an ionizer, improving its technical qualities compared to other similar products known in the state of the art, such as, for example, those already described.

The sheath will have a mesh of gold, silver, and graphite filament to increase its conductive capacity, which, together with the connection to the rest of the elements, improves its residual discharge and insulating capacity.

The connection to the earth connection of the dwelling will be made, in some embodiments, via a universal connection system (improved and adapted for discharge), incorporating two plastic connections and with only the earth connected, with a safety system for overloading the line.

The internal connections allow all the elements (topper, mattress, and bed base) to be continuously connected to each other, and their "joint" is connected to the earth of the house, therefore, with only one earth connection, the discharge is extended.

BRIEF DESCRIPTION OF THE FIGURE

The following is a very brief description of a series of drawings which help to better understand the invention, and which relate expressly to an embodiment of the invention which is presented as a non-limiting example of the invention.

FIG. 1 shows a schematic view of the earthed sleeping element of the dwelling.

DETAILED DESCRIPTION OF AN EMBODIMENT OF THE INVENTION

The attached FIGURES show an embodiment of the invention. More specifically, the rest element with earth connection of the dwelling, which is the subject of the present report, essentially comprises a toper or mattress topper (1), a bed base (2) and a latex mattress (3); said bed base (2) being made of laminated vaporized beech wood, varnished with 100% natural water-based varnish.

The mattress (3) is made of a core (4) of latex, composed of an emulsion of the resin of the Hevea *brasilensis* tree, 100% natural, beaten and baked in an oven at 120 degrees, without any chemical additives, which also incorporates an ionizing and anti-humidity layer (5) of steamed and pressed 100% natural coconut, incorporates an ionizing and anti-humidity film (5) of 100% natural steamed and pressed coconut, and inside it has a central layer (6) of pink salt rocks and white quartz rocks, as well as an antibacterial mesh (7) of bamboo thread.

In some embodiments, the ionizing and moisture-proof coconut sheet (5) is about 3 centimeters thick and is located at the bottom of the mattress, while the antibacterial mesh (7) made of bamboo thread and is incorporated into the mattress (3) between the latex core (4) and the ionizing and moisture-proof coconut sheet (5).

In any case, the mattress (3) also has a cover (8) made of a fabric made of 70% cashmere and 30% organic cotton, with a filling that covers at least the upper part of the mattress with a thickness of about 4 centimeters, made of 100% natural wool.

In addition, the sheath (8) incorporates a mesh of gold, silver and organic graphite and silver filament, which, together with the connection with the rest of the elements, improves its residual discharge and insulating capacity.

In an embodiment, the toper (1) will have a means of connection to the mattress (3) and this, in turn, to the bed base (2), which will finally be connected to the earth connection (10) of the dwelling through a universal connection system that incorporates a safety system to avoid overloading the line.

The bed base (2) will incorporate a series of titanium nails that will eliminate any residue through the earth connection of the dwelling. In a particular embodiment, between these nails and the bed base, an insulating and conductive tape (gold-graphene-silver) will be placed to eliminate all radiation.

The invention claimed is:

1. A resting element with connection to an earth connection of a dwelling, comprising:

a mattress topper;

a bed base and a latex mattress;

the bed base being made of laminated steamed beech wood, varnished with 100% natural water-based varnish, and a mattress made of a latex core, composed of an emulsion of a resin of a Hevea *brasilensis* tree, 100% natural, beaten and baked in an oven at 120 degrees Celsius, without any chemical additive, which, without any chemical additive, is made of latex, without any chemical additives, which, in addition, incorporates an ionizing and anti-humidity layer of 100% natural steamed and pressed coconut, with a central layer of pink salt rocks and white quartz rocks, as well as an antibacterial mesh of bamboo thread; and an external grounding conductor having free end that includes conductive material;

wherein the mattress, in addition, has a cover made of a fabric made of 70% cashmere and 30% organic cotton, with a filling that, at least, covers the upper part of the mattress with a thickness of about 4 centimeters, made of 100% natural wool and characterized in that the mattress topper has a means of connection to the mattress and this, in turn, to the bed base, the means of connection being a connector selected from the group consisting of a graphite element and a graphite body;

wherein a sheath of the line incorporates a mesh of gold, silver and organic graphite and silver filament which, together with the connection with the rest of the elements, improves a residual discharge and insulating capacity of the line;

wherein the mattress cover connects to the external grounding conductor; and wherein the bed base includes conductive tape to eliminate all radiations adjacent to the bed base.

2. A resting element with connection to an earth connection of a dwelling according to claim 1, where the ionizing and the anti-humidity sheet of coconut is about 3 centimeters thick and is placed in the lower part of the mattress, while the antibacterial mesh of bamboo thread is incorporated in the mattress between the core of latex and the the ionizing and anti-humidity sheet of coconut.

3. A resting element with connection to an earth connection of a dwelling according to claim 2, where the conductive tape includes gold, graphene, and silver.

4. A resting element with connection to an earth connection of a dwelling according to claim 2, wherein the means of connection is positioned on an edge of the bed base.

5. A resting element with connection to an earth connection of a dwelling according to claim 2, wherein the means of connection is positioned on a bottom of the mattress.

6. A resting element with connection to an earth connection of a dwelling according to claim 2, wherein the mattress includes an ionizer.

7. A resting element with connection to an earth connection of a dwelling according to claim 6, wherein the ionizer includes a plurality of antennas.

8. A resting element with connection to an earth connection of a dwelling according to claim 7, wherein the plurality of antennas are platinum antennas.

9. A resting element with connection to an earth connection of a dwelling according to claim 1, wherein the means of connection is positioned on an edge of the bed base.

10. A resting element with connection to an earth connection of a dwelling according to claim 1, wherein the means of connection is positioned on a bottom of the mattress.

11. A resting element with connection to an earth connection of a dwelling according to claim 1, wherein the mattress includes an ionizer.

12. A resting element with connection to an earth connection of a dwelling according to claim 11, wherein the ionizer includes a plurality of antennas.

13. A resting element with connection to an earth connection of a dwelling according to claim 12, wherein the plurality of antennas are platinum antennas.

* * * * *